United States Patent
Wolters et al.

(10) Patent No.: US 11,141,500 B1
(45) Date of Patent: Oct. 12, 2021

(54) ELECTRONIC DEVICE WITH UVC SANITIZING LIGHTS

(71) Applicants: Stephen Allen Wolters, Davenport, CA (US); Tiffany Suzanne Wolters, Davenport, CA (US)

(72) Inventors: Stephen Allen Wolters, Davenport, CA (US); Tiffany Suzanne Wolters, Davenport, CA (US)

( * ) Notice: Subject to any disclaimer, the term of this patent is extended or adjusted under 35 U.S.C. 154(b) by 0 days.

(21) Appl. No.: 17/034,836

(22) Filed: Sep. 28, 2020

Related U.S. Application Data

(60) Provisional application No. 63/038,703, filed on Jun. 12, 2020.

(51) Int. Cl.
    *A61L 2/10* (2006.01)
    *A61L 2/24* (2006.01)
    *A61L 2/26* (2006.01)

(52) U.S. Cl.
    CPC .......... *A61L 2/10* (2013.01); *A61L 2/24* (2013.01); *A61L 2/26* (2013.01); *A61L 2202/11* (2013.01); *A61L 2202/14* (2013.01)

(58) Field of Classification Search
    CPC ..... A61L 2/10; A61L 2/24; A61L 2/26; A61L 2202/11; A61L 2202/14
    See application file for complete search history.

(56) References Cited

U.S. PATENT DOCUMENTS

| | | | |
|---|---|---|---|
| 8,964,405 B2 | 2/2015 | Porte et al. | |
| 9,289,523 B2 | 3/2016 | Lee | |
| 9,468,695 B2 | 10/2016 | Liao et al. | |
| 2016/0000953 A1 | 1/2016 | Bettles et al. | |
| 2017/0080251 A1 | 3/2017 | Yehezkel | |
| 2020/0179718 A1* | 6/2020 | Gil | A61N 5/0624 |
| 2020/0188542 A1* | 6/2020 | Lei | A61L 2/08 |
| 2020/0371597 A1* | 11/2020 | Ueno | G06K 9/00355 |

* cited by examiner

*Primary Examiner* — Sean E Conley
(74) *Attorney, Agent, or Firm* — Boudwin Intellectual Property; Daniel Boudwin

(57) ABSTRACT

An electronic device with UVC sanitizing lights. The electronic device includes a housing having a display screen on a front side and an exterior assembly affixed to an opposing rear side. The exterior assembly includes a camera, a regular visible spectrum light, a sensor, and one or more UVC lights. The components of the exterior assembly are operably connected to a control module which facilitates user control of the exterior assembly components, particularly the UVC lights. The control module can include a software component that can be accessed using the electronic device's input controls and display screen. The control module allows the user to control the duration and intensity of an activation cycle of the UVC lights. The control module can further be utilized to prevent unauthorized individuals from activating the UVC lights. The UVC lights are utilized to destroy germs and other harmful contaminates on any desired surface.

1 Claim, 3 Drawing Sheets

ELECTRONIC DEVICE WITH UVC SANITIZING LIGHTS

CROSS REFERENCE TO RELATED APPLICATIONS

This application claims the benefit of U.S. Provisional Application No. 63/038,703 filed on Jun. 12, 2020. The above identified patent application is herein incorporated by reference in its entirety to provide continuity of disclosure.

BACKGROUND OF THE INVENTION

The present invention relates to devices for sanitizing surfaces utilizing UVC light. More specifically, the present invention provides an electronic device having an exterior assembly that includes one or more UVC lights, whereby the UVC lights are controllable via a software application that is accessible through the electronic device.

Ultraviolet (UV) light is one of the most effective known means for sanitizing surfaces. UV light is classified into different categories dependent upon wavelength. It has been demonstrated that exposing a surface to UV light in the range of 260 to 280 nanometers, referred to as UVC light, can destroy or render inert by the breakdown of DNA up to 99.9% of harmful viruses and bacteria on the surface. Germicidal UVC light has been used safely and efficiently in hospitals and laboratories for over 60 years. UVC light can be utilized to disinfect, sanitize, or sterilize a surface after prolonged exposure.

Despite its well-known effectiveness, Individuals currently lack a way to sanitize their own surroundings conveniently and effectively using UVC light. For the benefit of the health of an individual and of the general public, it is imperative that all individuals have the ability to minimize the effects of viruses, bacteria, mold, bed bugs, mites, fungi and spores that cause illness and spread infection. Such viruses and bacteria can be spread through surface contamination, as individuals frequently touch a contaminated surface and spread the contaminant to an orifice or mucous membrane, thereby causing illness in themselves or others. While proper sanitation of frequently used surfaces can minimize the spread of illness, having to utilize a separate UVC light rated for sanitizing purposes can be inconvenient. Therefore, a device that can easily and effectively sanitize a surface is desired.

Devices have been disclosed in the known art that relate to personal UVC disinfection devices. However, the devices in the known art have several drawbacks. For example, these devices are often bulky and difficult to handle or transport for a user, making it less likely that the devices will be properly and effectively utilized. Additionally, the devices in the known art fail to provide customization and control options for a UVC light array that can be easily accessed through the electronic device in which the UVC light is integrated. As one example of many, the devices disclosed in the known art lack a means for the user to control the duration, intensity, access, and other parameters of the UVC light.

In light of the devices disclosed in the known art, it is submitted that the present invention substantially diverges in design elements from the prior art and consequently it is clear that there is a need in the art for an improvement to existing UVC germicidal devices. In this regard the present invention substantially fulfills these needs.

SUMMARY OF THE INVENTION

In view of the foregoing disadvantages inherent in the known types of germicidal UVC devices now present in the prior art, the present invention provides an electronic device with UVC lights wherein the same can be utilized to sanitize a desired surface with UVC light. In one embodiment, an electronic device with UVC lights according to the present invention includes a housing having a display screen on a front side thereof and an exterior assembly disposed on a rear side of the housing. The exterior assembly includes a sensor, a camera, a standard light configured to emit light in the visible spectrum, and a UVC light configured to emit UVC light within a wavelength range between 260 nanometers and 280 nanometers.

The electronic device further includes a processor, a non-transitory computer readable medium operatively connected to the processor, and a logic stored in the non-transitory computer readable medium. When executed by the processor, the logic causes the electronic device to perform a method comprising the steps of determining an intensity setting for the UVC light, determining a duration setting for the UVC light, and determining an identity of a user. As one example, the user identity can be verified by comparing an image of the user recorded by the camera to a database of authorized user images, if the identity of the user matches an authorized user identity stored on the non-transitory computer readable medium, then the UVC light is activated at an intensity defined by the intensity setting and for a duration defined by the duration setting.

One object of the present invention is to provide an electronic device with UVC lights, wherein the intensity, duration, and other parameters of the UVC lights can be controlled through the electronic device itself via a software application.

Another object of the present invention is to provide an electronic device with UVC lights, wherein a sensor is configured to deactivate the UVC lights when it is detected that a living thing is within the beam path of the UVC light, for safety purposes.

A further object of the present invention is to provide an electronic device with UVC lights that only permits authorized users to activate the UVC lights, further increasing the safety of the system.

Other objects, features, and advantages of the present invention will become apparent given the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
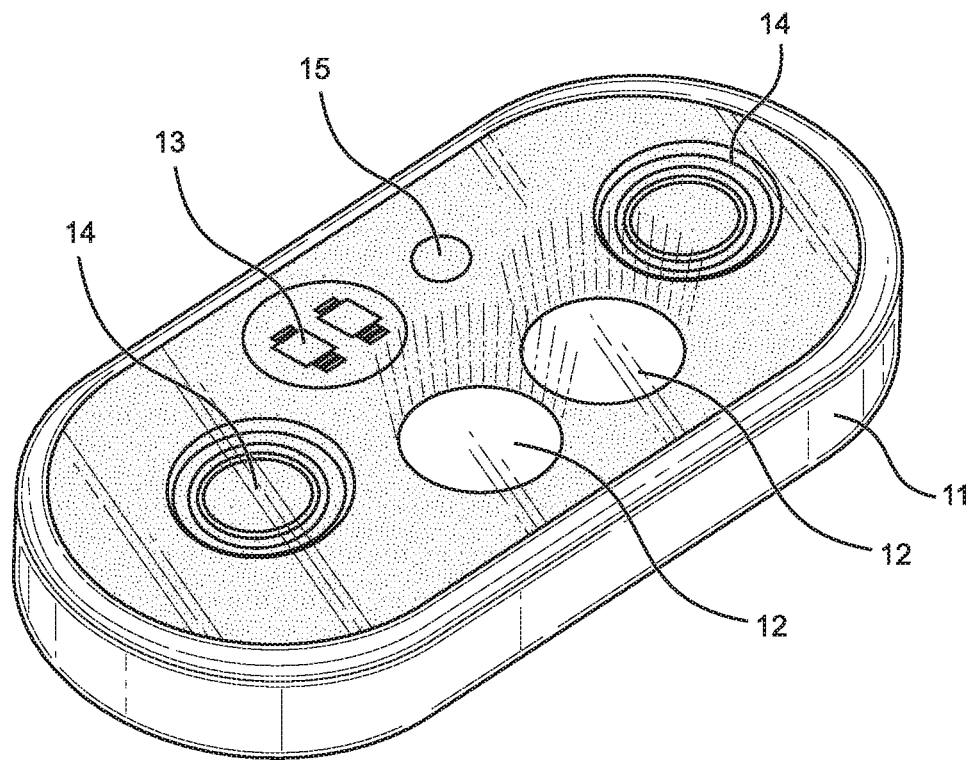
FIG. 1 shows a perspective view of the exterior assembly of an embodiment of the electronic device with UVC lights.

Reference is made herein to the attached drawings. Like reference numerals are used throughout the drawings to depict like or similar elements of the electronic device with UVC lights. For the purposes of presenting a brief and clear description of the present invention, the preferred embodiment will be discussed as used for sanitizing a desired surface via prolonged exposure to UVC light. The figures are intended for representative purposes only and should not be considered to be limiting in any respect.

According to some embodiments, the operations, techniques, and/or components described herein can be implemented as (i) a special-purpose computing device having specialized hardware and a logic hardwired into the computing device to persistently perform the disclosed operations and/or techniques or (ii) a logic that is implementable on an electronic device having a general purpose hardware processor to execute the logic and a computer-readable medium, e.g. a memory, wherein implementation of the logic by the processor on the electronic device provides the electronic device with the function of a special-purpose computing device.

In the interests of economy, the present disclosure refers to "a computer-readable medium," "a processor," and so on. However, this should not be read as limiting in any way as the present disclosure contemplates embodiments with the present invention utilizing "one or more computer-readable media," "one or more processors," and so on. Unless specifically limited to a single unit, "a" is intended to be equivalent to "one or more" throughout the present disclosure.

As referred to herein, the term "electronic device" refers to any computing device that includes at least a display screen and an input mechanism. The computing devices can be hard-wired to perform the operations, techniques, and/or components described herein, or can include digital electronic devices such as one or more application-specific integrated circuits (ASICs) or field programmable gate arrays (FPGAs) that are persistently programmed to perform the operations, techniques and/or components described herein, or can include one or more general purpose hardware processors programmed to perform such features of the present disclosure pursuant to program instructions in firmware, memory, other storage, or a combination. Such computing devices can also combine custom hard-wired logic, ASICs, or FPGAs with custom programming to accomplish the technique and other features of the present disclosure. The computing devices can be desktop computer systems, laptops, cell phones, tablets, networking devices, or any other device that incorporates hard-wired and/or program logic to implement the techniques and other features of the present disclosure.

Figure 4:
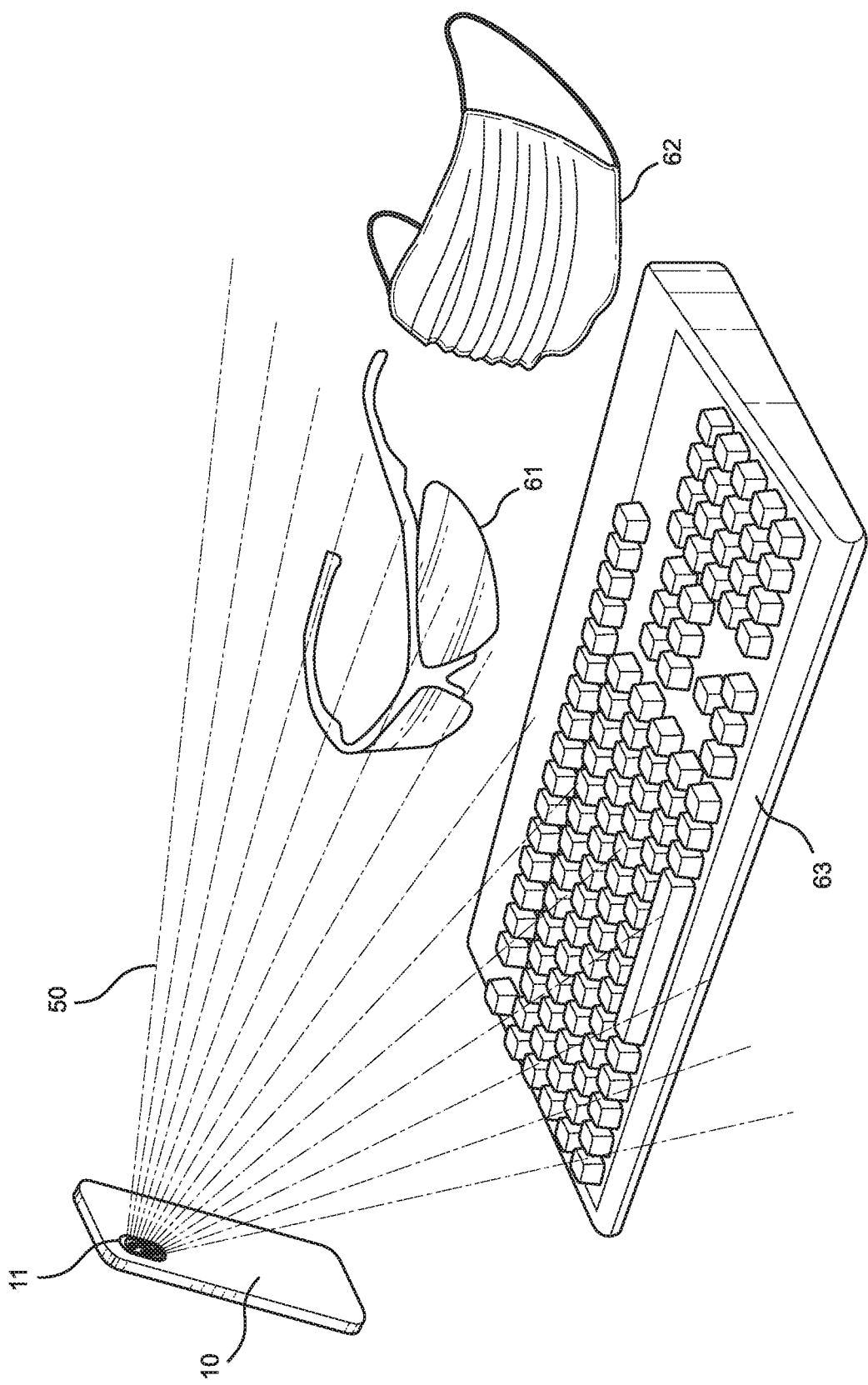
FIG. 4 shows a perspective view of an embodiment of the electronic device with UVC lights in use.

Referring now to FIG. 1, there is shown a perspective view of the exterior assembly of an embodiment of the electronic device with UVC lights. The exterior assembly 11 is attached to a rear side of the electronic device, as shown in FIG. 4. The exterior assembly 11 includes a camera 14 and a light 13 that can act as a flash for the camera or as an always-on flashlight type device. The exterior assembly 11 further includes at least one UVC light 12 that is configured to emit UVC light. In some embodiments, the UVC light 12 emits UVC light in the wavelength range between 260 nanometers and 280 nanometers. This wavelength range is the most effective at eradicating germs, bacteria, viruses, and other harmful contaminants. In some embodiments, the system includes a pair of UVC lights 12 to ensure greater coverage of an area when disinfecting the area. The UVC lights 12 can include a single light emitting diode that emits the UVC light. In another embodiment, the UVC light 12 can include a dual diode that can emit light in the visible spectrum as well as UVC wavelengths. In this embodiment, the UVC light 12 can also function as a flashlight or the flash for the camera 14 if needed.

In the shown embodiment, the exterior assembly 11 also includes a sensor 15. The sensor 15 can be utilized to detect the presence of an individual or living thing within the beam path of the UVC lights 12. In some embodiments, the sensor 15 is an infrared sensor that causes the UVC lights 12 to deactivate if a surface with a threshold temperature is detected. In another embodiment, the sensor 15 includes an accelerometer that can deactivate the UVC lights 12 if it is detected that the electronic device is moved at an upward angle toward the face of the user. In yet another embodiment, the camera 14 can include facial recognition capabilities and be configured to deactivate the UVC lights 12 if the face of an individual is detected. In this way, humans and other living things are kept safe from unnecessary exposure to the UVC light.

Figure 2:
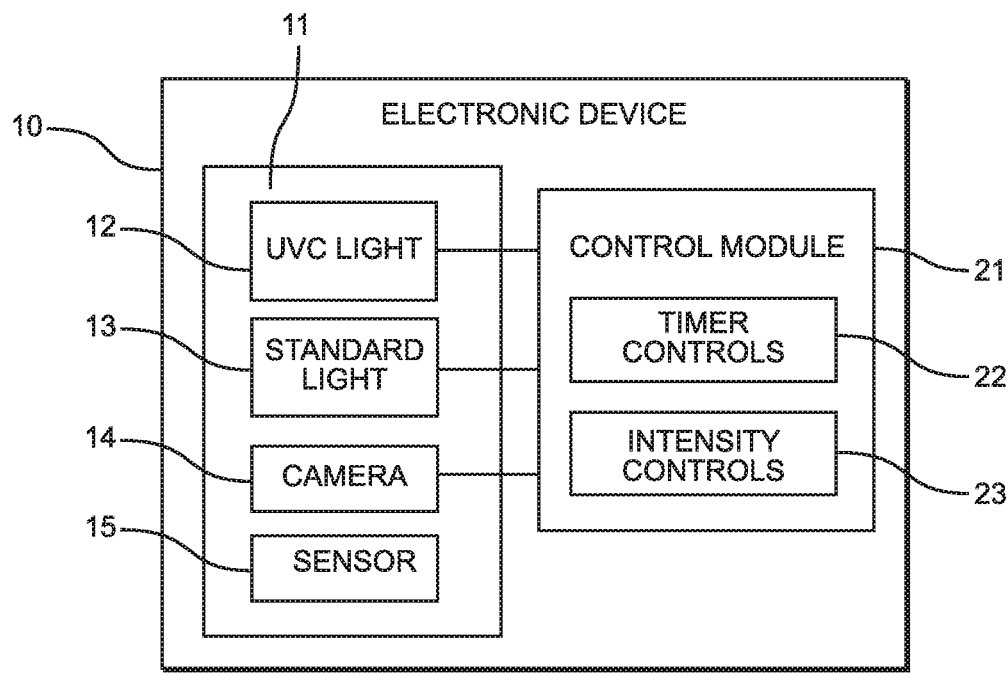
FIG. 2 shows a schematic diagram of the components of an embodiment of the electronic device with UVC lights.
Figure 3:
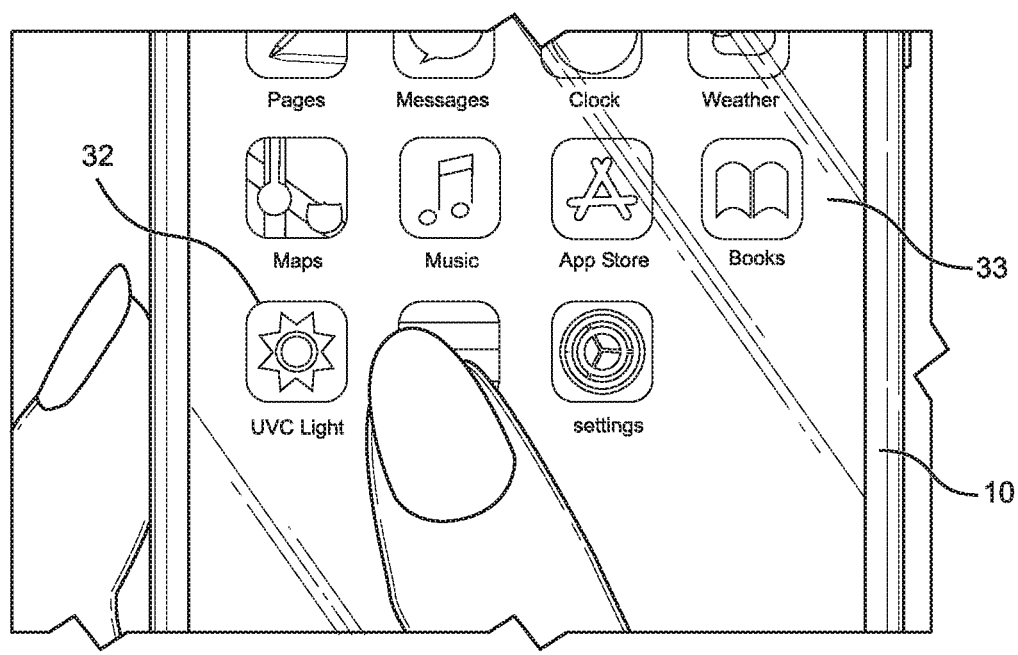
FIG. 3 shows a top plan view of an example graphical user interface of an embodiment of the electronic device with UVC lights.

Referring now to FIGS. 2 and 3, there is shown a schematic diagram of the components of an embodiment of the electronic device with UVC lights and a top plan view of an example graphical user interface of an embodiment of the electronic device with UVC lights, respectively. The electronic device 10 includes a control module 21 that is utilized to control the UVC light 12, the standard light 13, the camera 14, and the sensor 15. The components of the exterior assembly 11 are operably connected to the control module 21. The control module 21 can be a software component installed on a computer readable medium within the electronic device 10. The user can access the control module 21 via a graphical user interface 32 of a display screen 33 of the electronic device 10, as shown in FIG. 3. For example, in the shown embodiment, the display screen 33 includes a touch screen input mechanism. The control module 21 allows users to adjust the parameters of the UVC lights 12. For example, the control module 21 includes brightness or intensity controls 23 that allow authorized users to customize the strength of the emitted UVC radiation. Additionally, the control module 21 includes timer controls 22 that allow authorized users to control the duration for which the UVC lights 12 remain turned on after an initial activation. This provides authorized users with enhanced controls, allowing the UVC lights 12 to be more effective when used on particular types of surfaces or with surfaces having varying levels of contamination.

In some embodiments, the user of the electronic device 10 must be authenticated before the UVC light 12 can be activated. This prevents children or other unauthorized individuals from accidentally exposing themselves or others to UVC light. In one embodiment, the electronic device 10 includes identifying information of authorized users stored therein. The camera 14 can be utilized to record an image of the user. The control module 21 logic can then compare the recorded image to the database of stored images for a match. If a match is found, then the user is authorized and the UVC light 12 can activate. If a match is not found, then the user is determined to be unauthorized, and the UVC light 12 will not activate. In other embodiments, other user authentication methods may be utilized, such as a password input or a fingerprint scanner, for example.

Referring now to FIG. 4, there is shown a perspective view of an embodiment of the electronic device with UVC lights in use. In operation, the exterior assembly 11 of the electronic device 10 is oriented toward the object the user wishes to sanitize. When a desired object or surface is exposed to the emitted UVC radiation 50 at a high enough intensity for a long enough duration, the vast majority of unwanted contaminates are eradicated from the surfaces. In the illustrated example, the electronic device 10 is shown disinfecting a pair of sunglasses 61, a keyboard 63, and a facemask 62. However, there is no limit to the application of the UVC light and the user may disinfect any desired object or surface. The customizable timing and intensity parameters allow users to effectively eradicate germs, bacteria, viruses, and the like from different types and sizes of surfaces or objects. The authentication mechanism prevents children and other unauthorized individuals from accidentally injuring themselves with the UVC radiation, while the automated deactivation of the UVC lights in certain situations further enhances safety. In this way, the present invention provides enhanced structure, improved functional capabilities, and improved safety from any existing UVC emitting devices.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An electronic device, consisting of:
a housing having a display screen on a front side thereof;
an exterior assembly disposed on a rear side of the housing, the exterior assembly consisting of:
   a pair of cameras positioned toward a front end and a rear end of the exterior assembly;
   a sensor positioned between the one or more cameras;
   a standard light positioned on a first side of the exterior assembly and configured to emit light in the visible spectrum; and
   a UVC light configured to emit light having a wavelength range between one hundred nanometers and two hundred eighty nanometers, the UVC light positioned between the camera on a side of the exterior assembly opposing the standard light;
a control module including a processor, a non-transitory computer readable medium operatively connected to the processor, and a logic stored in the non-transitory computer readable medium that, when executed by the processor, causes the electronic device to perform a method, the method comprising:
determining an intensity setting for the UVC light;
determining a duration setting for the UVC light;
determining an identity of a user;
if the identity of the user matches an authorized user identity stored on the nontransitory computer readable medium, then activating the UVC light at an intensity defined by the intensity setting and for a duration defined by the duration setting; and
if either one of the sensor or the pair of cameras detects that a living thing is located within a beam path when the UVC light is activated, then deactivating the UVC light.

* * * * *